US006998259B1

(12) United States Patent
Davis et al.

(10) Patent No.: US 6,998,259 B1
(45) Date of Patent: Feb. 14, 2006

(54) ENZYMATIC TREATMENT OF WHEY PROTEINS FOR THE PRODUCTION OF ANTIHYPERTENSIVE PEPTIDES AND THE RESULTING PRODUCTS

(75) Inventors: Martin E. Davis, Tonka Bay, MN (US); Anand Rao, Savage, MN (US); Sylvie Gauthier, Charny (CA); Yves Pouliot, Charny (CA); Line Gourley, Québec (CA); Anne-Francoise Allain, Saint-Lambert de Lauzon (CA)

(73) Assignee: Davisco Foods International, LeSueur, MN (US)

( * ) Notice: Subject to any disclaimer, the term of this patent is extended or adjusted under 35 U.S.C. 154(b) by 0 days.

(21) Appl. No.: 09/702,068

(22) Filed: Oct. 30, 2000

Related U.S. Application Data

(63) Continuation of application No. 09/359,201, filed on Jul. 22, 1999, now abandoned.

(60) Provisional application No. 60/135,080, filed on May 20, 1999.

(51) Int. Cl.
C12P 21/06 (2006.01)
C12N 9/60 (2006.01)
A01N 37/18 (2006.01)

(52) U.S. Cl. .......................... 435/219; 435/68.1; 514/2
(58) Field of Classification Search ............... 435/68.1, 435/219; 514/2
See application file for complete search history.

(56) References Cited

U.S. PATENT DOCUMENTS

| | | |
|---|---|---|
| 3,857,966 A | 12/1974 | Feldman et al. ............... 427/7 |
| 3,932,612 A | 1/1976 | Pour-El et al. ............... 426/46 |
| 3,970,520 A | 7/1976 | Feldman et al. ............... 195/29 |
| 4,001,437 A | 1/1977 | Jaeggi et al. .................. 426/34 |
| 4,107,334 A | 8/1978 | Jolly ............................. 426/7 |
| 4,154,675 A | 5/1979 | Jewett et al. .................. 210/33 |
| 4,218,490 A | 8/1980 | Phillips et al. ............... 426/549 |
| 4,293,571 A | 10/1981 | Olofsson et al. ............... 426/7 |
| 4,293,583 A | 10/1981 | Farr et al. .................... 426/657 |
| 4,427,658 A | 1/1984 | Maubois et al. ............. 424/177 |
| 4,482,574 A | 11/1984 | Lee .............................. 426/7 |
| 4,486,413 A | 12/1984 | Wiesenberger et al. ...... 426/177 |
| 4,847,096 A | 7/1989 | Mellqvist et al. ............. 426/41 |
| 4,981,704 A | 1/1991 | Thibault ....................... 426/41 |
| 5,039,532 A | 8/1991 | Jost et al. ..................... 426/41 |
| 5,322,773 A | 6/1994 | Kaneko et al. ............. 435/68.1 |
| 5,369,015 A | 11/1994 | Yoshikawa et al. ........ 435/68.1 |
| 5,405,637 A | 4/1995 | Martinez et al. ............. 426/580 |
| 5,589,357 A | 12/1996 | Martinez et al. ........... 435/68.1 |
| 5,695,796 A | 12/1997 | Yamamoto et al. ........... 426/43 |
| 5,744,179 A | 4/1998 | Shimamura et al. ........... 426/41 |
| 5,854,029 A | 12/1998 | Yamamoto .................. 435/71.2 |
| 5,869,444 A | 2/1999 | Klein ............................. 514/2 |
| 5,882,705 A | 3/1999 | Sato et al. ..................... 426/41 |
| 5,952,193 A | 9/1999 | Shimamura et al. .......... 435/68 |
| 6,630,320 B1 | 10/2003 | Davis et al. .................. 435/24 |

FOREIGN PATENT DOCUMENTS

| | | |
|---|---|---|
| EP | 0 474 506 B1 | 5/1998 |
| JP | 04082898 A | 3/1992 |
| JP | 04282398 | 10/1992 |
| JP | 04282400 A | 10/1992 |
| JP | 06345664 | 12/1994 |
| JP | 08269088 A | 10/1996 |
| WO | 99/65326 | 12/1999 |

OTHER PUBLICATIONS

Hawley's Condensed Chemical Dictionary, Lewis, Sr., 13th Edition, 1997, p. 937.*
Abubakar, A. et al; "New Derivation of the Inhibitory Activity Against Angiotensin Converting Enzyme (ACE) from Sweet Cheese Whey"; *Tohoku J. Agri. Res.* vol. 47 No. 1-2, Sep. 1-8, 1996.
Abubakar, A. et al; "Structural analysis of New Antihypertensive Peptides Derived from Cheese Whey Protein by Proteinase K Digestion"; *J. Dairy Sci.* 81:12, 3131-3138; 1996.
Cushman, D. W. et al; "Spectrophotometric Assay and Properties of the Angiotensin-Converting Enzyme of Rabbit Lung"; *Biochem Pharmacol* 20: 163 7-1648; 1971.
Ferreira, S.H., et al; "Isolation of Bradykinin-Pptentiating Peotides from *Bothrops* jararaca Venom"; *Biochemistry*, vol. 9, No. 13; 1970.
Kohmura, M., et al; "Inhibition of Angiotensin-converting Enzyme by Synthetic Peptides of Human β-Casein", *Agri. Biol. Chem.* 53(8). 2107-2114; 1989.
Maruyama, S., et al.; "A Peptide Inhibitor of Agiostensin I Converting Enzyme in the Tryptic Hydrolysate of Casein"; *Agri. Biol. Chem.* 46(5); 1393-1394, 1982.
Maubois, J.L., et al; "Les peptides du lait à activité physiologique III. Peptides du lait è effet cardiovasculaire: activités antithrombotique et antihypertensive", *Lait*, 71: 249-255.
Mullally, M. M., et al; "Identification of a novel angiotensin-I-converting enzyme inhibitory peptide corresponding to a tryptic fragment of bovine β-lactoglobulin"; *FEBS Letters*, 402:99-101.

(Continued)

Primary Examiner—Michael Meller
(74) Attorney, Agent, or Firm—Kagan Binder, PLLC

(57) ABSTRACT

Enzymatic digests of whey protein concentrates were prepared using animal, bacterial and fungal proteases, and evaluated for antihypertensive activities. The highest ACE-inhibitory activity was obtained with the purified peptide β-1g (f142–148) obtained by chemical synthesis, for which an $IC_{50}$ value of 0.04 mg powder.ml$^{-1}$ was found. The hydrolysates derived from BiPRO™ whey protein isolate and β-1g both gave higher antihypertensive activities ($IC_{50}$ values of 0.29 to 0.90 mg powder.ml$^{-1}$) than the other hydrolysates tested ($IC_{50}$ values of 0.96 and 1.30 mg powder.ml$^{-1}$). The recovered hydrolysate can be used to treat hypertension in mammals such as humans and domestic pets such as dogs and cats.

36 Claims, No Drawings

OTHER PUBLICATIONS

Oshima, G., et al; Peptide Inhibitors of Angiotension-I-Converting Enzyme in Digests of Gelatin by Bacterial Collagenase; *Biochimica et Biophysica Acta* 566, 128-137, 1979.

Pearce R. J.; "Whey Protein Recovery and Whey Protein Fractionation"; *Whey and Lactose Processing*; J.G. Zadow, ed., Elsevier, 271-316, London.

Takano, Toshiaki; "Milk Derived Peptides and Hypertension Reduction"; *Int. Dairy Journal* 8 (1980) 375-381; Great Britain.

"Antihypertensive Effects of Whey Protein Hydrolysates in Rats Reduces Mean Arterial Blood Pressure", *Davisco Press Release*, (2000).

"Davisco Foods International, Advitech Solutions Join Forces to Produce Whey Protein Hydrolysates", *Davisco Press Release*, (1998).

"Davisco Nominated for Prestigious International Award for its Patented Hypertension-Reducing Whey Protein", *Davisco Press Release*, (1999).

Ju et al., "Effects of Limited Proteolysis on Gelation and Gel Properties of Whey Protein Isolate", *Journal of Dairy Science*, 78, 2119-2128 (1995).

Laragh, "L'hypertension", *La Recherche*, 10, 1068-1076 (1979). (abstract).

Otte et al., "Effects of Limited Proteolysis on the Microstructure of Heat-Induced Whey Protein Gels at Varying pH", *Journal of Dairy Science*, 79, 782-790 (1996).

\* cited by examiner

ENZYMATIC TREATMENT OF WHEY PROTEINS FOR THE PRODUCTION OF ANTIHYPERTENSIVE PEPTIDES AND THE RESULTING PRODUCTS

CROSS REFERENCE TO RELATED APPLICATIONS

This application is a continuation of U.S. patent application Ser. No. 09/359,201, filed Jul. 22, 1999, abandoned, which claims the benefit of priority to U.S. Provisional Patent Application Ser. No. 60/135,080, filed May 20, 1999.

BACKGROUND OF THE INVENTION

The invention relates to a method for suppressing angiotensin-converting enzyme (ACE), a composition effective for this purpose and a method for preparing the composition, specifically by enzymatic conversion of whey proteins.

Hypertension has been reported to be the most important cause of human deaths in industrialized countries. (See, for example, Laragh, J. H., 1979. L'hypertension. Recherche, 105 (10): 1068–1076.) Nearly 30% of the fatalities among adults would result from hypertension or from its renal, coronary or neurological complications. The elucidation of the physiological mechanisms responsible for hypertension has lead the pharmaceutical industry to propose angiotensin converting enzyme (ACE)—inhibitory substances. ACE catalyses the degradation of angiotensin I into angiotensn II, a strong vasoconstrictor.

Peptides found in Brazilian snake venom have been identified as the most effective natural substance for the inhibition of ACE. (See, Ferreira, S. H., Bartelt, D.C., Greene, L. J., 1970. Isolation of bradykinin-potentiating peptides from Bothrops jararaca venom. Biochemistry, 9 (13): 2583–2593.) The inhibitory effect of natural peptides has been related to their binding at the active site of ACE. (See, Maubois, J. L., Léonil, J., Trouvé, R. Bouhallab, S., 1991. Les peptides du lait á activité physiologique III. Peptides du lait á effet cardiovasculaire: activités antithrombotique et antihypertensive. Lait, 71: 249–255.)

A structure-function study of these various bioactive peptides has suggested that they often possess a Pro-Pro, Ala-Pro or Ala-Hyp at their C-teminal sequence. (See, Maruyama, S., Suzuki, H., 1982. A peptide inhibitor of angiotensin I converting enzyme in the tryptic hydrolysate of casein. Agric. Biol. Chem., 46 (5): 1393–1394; and Oshima, G., Shimabukuro, H., Nagasawa, K. 1979. Peptide inhibitors of angiotensin I-converting enzyme in digests of gelatin by bacterial collagenase. Biochim. Biophys. Acta, 566: 128–137.) The occurrence of proline might also contribute to the ACE-inhibitory activity of peptides derived from food proteins. (See, Kohmura, M., Nio, N., Kubo, K., Minoshima, Y., Munekata, E., Ariyoshi, Y. 1989. Inhibition of angiotensin-converting enzyme by synthetic peptides of human β-casein. Agric. Biol. Chem., 53 (8): 2107–2114.)

Maruyama and Suzuki [supra] have evidenced such amino acid sequences in peptides from tryptic casein hydrolysates. The authors have shown that the peptide f23–34 from $x_{sI}$ casein (bovine, variant B), possesses ACE-inhibitory activity estimated by an $IC_{50}$ value (concentration needed to inhibit 50% ACE activity) of 77 μM. Numerous other studies followed this work and revealed other ACE-inhibitory peptides in casein hydrolysates. In a recent review, Nakano has reported the occurence of 18 distinct milk protein-derived peptide sequences, found in sour milk, and which have been shown to possess ACE-inhibitory activity. (Nakano, T., 1998, Milk derived peptides and hypertension reduction. Int. Dairy J., 8: 375–381.)

However, only a few studies have reported the occurrence of ACE-inhibitory activities among whey proteins hydrolysates. Abubakar, et al., have determined the ACE-inhibitory activity in whey protein hydrolysates using seven different enzymes: trypsin, proteinase-K, actinase-E, thermolysin, papain, pepsin and chymotrypsin. It was shown that the specificity of the enzyme had a pronounced effect on the resulting ACE-inhibitory activity of the hydrolysate, and that the biological activity was originating from the major whey proteins (β-1g, α-1a, BSA, Ig) and not from the caseinomacropeptide. (Abubakar, A., Saito, T., Aimar, M. V., Itoh, T. 1996. New derivation of the inhibitory activity against angiotensin converting enzyme (ACE) from sweet cheese whey. Tohoku J. Agric. Res., 47 (1–2): 1–8.) More recent work from. Abubakar, et al., has allowed the identification of nine peptide sequences, namely β2-microglobulin (f18–20), β -lactoglobulin (f78–80), serum albumin (f221–222), β-casein (fV–61, f59–64, f62–63, f80–90, f157–158, f205–206), among which β-lactoglobulin (f78–80) showed the strongest antihypertensive activity in spontaneously hypertensive rats. (Abubakar, A., Saito, T., Kitazawa, H., Kawai, Y., Itoh, T., 1998, Structural analysis of new antihypertensive peptides derived from cheese whey protein by proteinase K digestion. J Dairy Sci., 12: 3131–3138.) Finally, Mullaly et al., have demonstrated that a peptidic fraction, isolated by using RP-HPLC, from a tryptic hydrolysate prepared with bovine β-lactoglobulin had an $IC_{50}$ value of 159.8 μmol/L, compared to Captopril, a commercial drug commonly used in hypertension treatment, which has an $IC_{50}$ of 0,006 μmol/L. (Mullally, M. M., Meisel, H., FitzGerald, R. J., 1997. Identification of a novel angiotensin-I-converting enzyme inhibitory peptide corresponding to a tryptic fragment of bovine β-lactoglobulin. FEBS Letters, 402: 99–101.) Mass spectrometry analyses have allowed the identification of peptide f142–148 from β-lactoglobulin as being responsible for the ACE-inhibitory activity in tryptic hydrolysates of β-lactoglobulin. The same peptidic sequence obtained by chemical synthesis showed an $IC_{50}$ of 42.6 μmol/L.

SUMMARY OF THE INVENTION

It is an object of the invention to provide improvements in the field of suppressing angiotensin-converting enzyme (ACE).

It is an object of the invention to provide a method for suppressing angiotensin-converting enzyme.

It is another object of the invention to provide a composition effective for suppressing angiotensin-converting enzyme.

It is yet another objective of the invention to provide a method for preparing a composition effective for suppressing angiotensin-converting enzyme, specifically by enzymatic conversion of whey proteins.

These and other objects are accomplished by the invention, by improvements which enable the production of an ACE-suppressing composition by the hydrolysis of whey protein hydrolysate, the recovery of the ACE-suppressing composition, and a regimen for use of the ACE-suppressing composition.

The process for preparing the ACE-suppressing composition comprises: preparing an aqueous solution of whey protein isolate and a proteolytic enzyme; holding said solution under conditions effective to partially hydrolyze said whey protein isolate to provide a hydrolysate having increased ACE-suppressing activity in mammals; and recovering said hydrolysate from said solution. The proteolytic enzyme is inactivated as necessary, preferably by heating. The hydrolysate is preferably dried for use in a regimen which comprises oral administration to a mammal, such as a human or a domestic pet such as a dog or cat, in amounts and at intervals effective to suppress ACE-activity. Many of the preferred aspects of the invention are described below.

DETAILED DESCRIPTION OF THE INVENTION

Whey protein isolates (WPI) can be obtained from commercial-scale fractionation of cheese whey by various processes, including ion-exchange processing using cationic and/or anionic resins selected for the intended functionality of the isolate. (Pearce, R. J., 1992, Whey protein recovery and whey protein fractionation, In *Whey and Lactose Processing*, J G Zadow, Ed., Elsevier, London, 271–316.) Commercial WPI products issued from ion-exchange processing, such as BiPRO™ (Davisco Foods International, LeSueur, Minn.), are characterized by a high protein content (>94% w/w), low ash content (<3%), traces (<1%) of fat and lactose. The protein distribution of a typical WPI shows 73% $\beta$-lactoglobulin, 15% $\alpha$-lactalbumin, and the remaining 12% is composed of bovine serum albumin, immunoglobulins and caseinomacropeptide.

BiPRO™ whey protein isolate is the preferred source of whey protein isolate for use in the invention and is available from Davisco Foods International, Inc., with offices at 11000 W. 78th Street, Suite 210, Eden Prairie, Minn. 55344. The preferred BiPRO™ whey protein isolate has a (PDCAAS) Protein Digestibility Corrected Amino Acid Score of 1.14. The fat and lactose levels are less than 1%. The BiPRO™ whey protein isolate is prepared by ion-exchange technology, and contains about 91% (w/w) $\beta$-lactoglobulin. Preferably, the whey protein isolate employed according to the invention will contain at least 70% and preferably at least 80%, e.g., 85–95%, $\beta$-lactoglobulin, with the remaining comprising $\alpha$-lactalbumin, serum albumin, immunoglobulins and caseinomacropeptide. BiPRO™ is essentially undenatured and is fully soluble over the pH range 2.0 to 9.0, and has the following analysis:

| Analysis* Method | Specification | Typical Range | Test |
|---|---|---|---|
| Moisture (%) | 5.0 max. | 4.7 ± 0.2 | Vacuum Oven |
| Protein, dry basis (N x 6.38)(%) | 95.0 min. | 97.5 ± 1.0 | Combustion |
| Fat (%) | 1.0 max. | 0.6 ± 0.2 | Mojonnier |
| Ash (%) | 3.0 max. | 1.7 ± 0.3 | Gravimetric |
| Lactose (%) | 1.0 max. | <0.5 | by difference |
| pH | 6.7–7.5 | 7.0 ± 0.2 | 10% Sol. @ 0° C. |

*All results reported "AS IS" basis except where noted.
Standard Methods for the Examination of Dairy Products, 16th Edition.

As noted, whey protein isolates other than BiPRO™ can be employed and where used preferably have similar analyses to that above, varying by from 0 to 25%, e.g., from 5 to 10%, or less, from the above Typical Range values. A suitable whey protein isolate can be produced having similar properties through a selective ion exchange process that selects the primary functional proteins—beta-lactoglobulin and alpha-lactalbumin—for concentration and spray drying. Such a process is described in U.S. Pat. No. 4,154,675 to Jowett, et al.., and U.S. Pat. No. 4,218,490 to Phillips, et al. If properly produced, whey protein fractions having lower protein contents, e.g., as low as 35%, might be employed. In addition, $\beta$-1g produced by ion exchange separation can also be employed, but is less preferred than the BiPRO™ whey protein isolate.

On a more detailed analysis of BiPRO™ whey protein isolate, the following is found for each 100 grams of whey protein isolate:

| Component | |
|---|---|
| Calories | 374 |
| Calories From Total Fat | 3 |
| Total Fat (g) | 0.3 |
| Saturated Fat (g) | 0.2 |
| Cholesterol (mg) | 10 |
| Sodium (mg) | 600 |
| Potassium (mg) | 120 |
| Total Carbohydrates (g) | 0 |
| Dietary Fiber (g) | 0 |
| Sugars (g) | 0 |
| Protein (g) | 93 |
| Vitamin A (IU) | 20 |
| Vitamin C (mg) | 2.0 |
| Calcium (mg) | 120 |
| Iron (mg) | 5 |
| Phosphorus (mg) | 25 |
| Magnesium (mg) | 15 |
| Ash (g) | 2 |
| Moisture (g) | 5 |

And, to provide an amino acid profile of the preferred BiPRO™ whey protein isolate, samples were subjected to drying for 24 hours in a dessicator over phosphorous pentoxide and sodium hydroxide. The dry samples were hydrolyzed in HC1I vapor (6N HC1 with 1% phenol and 0.5% sodium sulfite) under Argon atmosphere. After 20 hours of hydrolysis at 110 degrees Celsius, the samples were dissolved in 200 ul of Beckman Na—S sample buffer. This acid hydrolysis method destroys tryptophan.

Analyses were conducted on a Beckman 6300 Amino Acid Analyzer. Norleucine was used as an internal standard. The analysis showed the following:

| | Grams Amino Acid Per | |
|---|---|---|
| Amino Acid | 100 g protein | 100 g powder |
| Alanine | 7.6 | 7.01 |
| Arginine | 2.0 | 1.84 |
| Aspartate | 10.1 | 9.31 |
| Cysteine/Cystine | 4.3 | 3.96 |
| Glutamine | 14.3 | 13.18 |
| Histidine | 1.6 | 1.48 |
| Isoleucine* | 5.4 | 4.98 |
| Leucine* | 13.7 | 12.63 |
| Lysine* | 9.6 | 8.85 |
| Methionine* | 2.4 | 2.21 |
| Phenylalanine* | 3.1 | 2.86 |
| Proline | 4.5 | 4.14 |
| Serine | 4.90 | 4.52 |
| Threonine* | 5.30 | 4.89 |
| Tyrosine | 2.90 | 2.67 |
| Valine* | 5.60 | 5.16 |
| Totals | 100.10 | 92.29 |

*Essential Amino Acids

Again, when whey protein isolates other than BiPRO™ are employed, they preferably have similar analyses to that above, varying by from 0 to 25%, e.g., from 5–10%, or less, from the above values.

Enzymatic digests of BiPRO™ and of commercial β-1g-rich product were prepared using animal, bacterial and fungal proteases, in order to determine the potential of these commercial substrates for the preparation of peptide mixtures having antihypertensive activities. The objective of the work was to determine the ACE-inhibitory activity of various hydrolysates generated by enzymatic hydrolysis from whey protein isolates obtained by ion-exchange chromatography, in comparison with other commercially-available whey protein hydrolysates.

Materials and Methods

Whey protein hydrolysate WPH 917 (84.5% protein w/w) was obtained from New Zealand Milk Product Inc. (Santa Rosa, USA). Whey protein hydrolysate LE80GF (80.0% w/w) was obtained from DMV International (New-York, USA). Whey protein isolate (BiPRO™) and β-lactoglobulin-rich product were obtained from Davisco Foods International (Le Sueur, Minn., USA). Purified peptidic sequence Ala-Leu-Pro-Met-His-Ile-Arg modelling the peptide f-142–148 from β-1g was chemically-synthetized by the Service de séquence de peptides de l'Est du Québec (Ste-Foy, Qc, Canada). HEPES Sodium salt, Hippuryl-L-Histidyl-L-Leucine, and Angiotensin Converting Enzyme (from rabbit lung) were purchased from Sigma Chemical Co. (St. Louis, USA). All other products used were analytical grade.

Whey proteins (BiPRO™ or β-1g) were solubilized at 20% W/V, adjusted to pH 8.0 or 8.5 by using a mixture of NaOH and KOH 4N and maintained at temperatures between 40° C. and 50° C. corresponding to the optimal temperature of the enzymes used. Table 1 reports the characteristics of the enzymes used for the preparation of the enzymatic hydrolysates for the study. BiPRO™ and β-1g-rich product were utilized for the preparation of 601 and 605, but only Bipro™ was used for 603K. The protein solutions were incubated with the proteases at an enzyme: substrate ratio of 1:800 for AS-601, 1:50 for AS-603K and 1:100 for AS-605K. The enzymatic hydrolysis was performed under pH-stat conditions until a degree of hydrolysis (DH) of 5.5–6.5% for AS-601 and under a combination of pH-stat and osmometry methods until a DH of 11.0–12.5% for AS-603K, and a DH of 19.5–20.5% for AS-605K. The hydrolysis reaction was stopped at the selected DH values by means of heat treatment (75 to 85° C. for 15 s) in a plate heat exchanger to inactivate the enzyme and followed by cooling and storage at 5–10 ° C. until further processing. The resulting hydrolysates were further spray dried and handled as powdered ingredient. Fractions can be taken based on molecular weight and tested for relative activity, with the most active fractions selected.

A typical analysis for the AS-601K and AS-603K products prepared from BiPRO™ whey protein hydrolysate are given below.

| Analysis* (AS-601K) | Specification | Typical Range | Test Method |
|---|---|---|---|
| Moisture (%) | 5.0 max. | 4.0 ± 0.5 | Vacuum Oven |
| Total Nitrogen (TN), % | 14.1 min. | | Combustion |
| Protein dry basis (N x 6.38)(%) | 90.0 min. | 91.0 ± 0.5 | Calculated |
| Amino Nitrogen (AN), % | 1.7 min. | | Formol Titration |
| AN/TN, % | 12.0 min. | 12.0–15.0 | Calculated |
| Degree of Hydrolysis, % | 5.0 min. | 5.5–6.5 | OPA Method |
| Fat (%) | 1.0 max | <1.0 | Mojonnier |
| Ash (%) | 6.0 max. | 5.5 ± 0.3 | Standard** |
| Lactose (%) | 1.0 max. | <1.0 | by difference |
| pH | 8.5 max. | 8.0 ± 0.2 | 10% Sol. @ 20° C. |

| Molecular Weight Profile (HPLC) | Range (Daltons) | Soluble Peptides*** |
|---|---|---|
| | >5000 | 50–55% |
| | 2000–5000 | 15–20% |
| | <2000 | 30–35% |

| Analysis*(AS-603K) | Specification | Typical Range | Test Method |
|---|---|---|---|
| Moisture (%) | 5.0 max. | 4.0 ± 0.5 | Vacuum Oven |
| Total Nitrogen (TN), % | 14.1 min. | | Combustion |
| Protein, dry basis (N x 6.38) % | 94.0 min. | 95.0 ± 0.5 | Calculated |
| Amino Nitrogen (AN), % | 2.2 min. | 2.4 ± 0.2 | Formol Titration |
| AN/TN, % | 15.8 min. | 16.3 ± 0.5 | Calculated |
| Degree of Hydrolysis, % | 7.7 min. | 8.7 ± 1.0 | OPA Method |
| Fat (%) | 1.0 max. | <1.0 | Mojonnier |
| Ash (%) | 5.0 max. | 3.5 ± 0.3 | Gravimetric |
| Lactose (%) | 1.0 max. | <1.0 | by difference |
| pH | 7.5 max. | 7.0 ± 0.2 | 10% Sol. @ 20° C. |
| Scorched Particles | 15 mg/25 g max. | 7.5 mg | ADPI |

| Molecular Weight Profile (HPLC) | Range (Daltons) | Peptides |
|---|---|---|
| | >10,000 | 30–35% |
| | 5000–10,000 | 10–15% |
| | 2000–5000 | 25–30% |
| | <2000 | 25–30% |

*All results reported "AS IS" basis except where noted.
**Standard Methods for the Examination of Dairy Products, 16th Edition.
***Percent of total soluble peptides in 0.45 μ filtrate.

TABLE 1

Characteristics of the enzyme sources used for the preparation of hydrolysates

| Enzyme (Name, Supplier) | Source | Optimal pH | Temp. (° C.) | Hydrolysate |
|---|---|---|---|---|
| Trypsin VI Trypsin Activity 2,400 U/mg minimum | Porcine | 8.0 | 37 | AS-601 (BiPRO ™) |

TABLE 1-continued

Characteristics of the enzyme sources used for the preparation of hydrolysates

| Enzyme (Name, Supplier) | Source | Optimal pH | Temp. (° C.) | Hydrolysate |
|---|---|---|---|---|
| Chymotrypsin activity 350 U/mg minimum Canadian Innovatech Inc Abbotsford, BC, Canada | | | | AS-601 (β-1 g) |
| Protease P Amano-6 Proteinase activity 60,000 units/g minimum Amano, Enzyme Co. Ltd Rochester, IL, USA | Fungal | 7.5 | 45 | AS-605K (BiPRO ™) AS-605K (β-1 g) |
| Multifect Activity 3,000 GSU/ml minimum (Note: GSU is Genencor Subtlisin Units - developed internally by Genencor) Genencor International Rochester, NY, USA | Bacterial | 8.5 | 50 | AS-603K (BiPRO ™) |

Determination of ACE-Inhibitory Activity

The ACE-inhibitory activity was measured in vitro by a spectrophotometric assay according to the method of Cushman and Cheung. (Cushman, D. N., Cheung, H. S. 1971 Spectrophotometric assay and properties of the angiotensin converting enzyme of rabbit lung. Biochemical Pharmacology, 20: 1637–1648.) According to this method, hippuric acid is liberated from hippuryl-L-histidyl-L-leucine (HHL) by the enzymatic reaction of ACE. After extraction by ethyl acetate and removal of ethyl acetate by heat evaporation, hippuric acid is dissolved in deionized water.

TABLE 2

Assay conditions for the measurement of ACE-inhibitory activity

| Reagent volumes (μl) | Sample | Control | Blank |
|---|---|---|---|
| Substrate solution[1] | 200 | 200 | 200 |
| Sample solution[2] | 50 | — | — |
| HEPES-HCl Buffer[3] | — | 50 | 50 |
| Deionized water | 20 | 20 | 20 |
| | mixed using vortex and equilibrated to 37° C. | | |
| Stopping solution[4] | — | — | 300 |
| ACE solution[5] | 30 | 30 | 30 |
| | mixed using vortex and incubated at 37° C. for 20 min | | |
| Stopping solution | 300 | 300 | — |
| Total volume (μl) | 600 | 600 | 600 |

[1]HHL was dissolved in HEPES-HCl Buffer to obtain a final concentration of 0.3% (w/v).
[2]Samples were diluted at the appropriate concentration with HEPES-HCl Buffer.
[3]HEPES Sodium Salt (50 mM) with 300 mM NaCl, pH adjusted at 8.3 with 1 M HCl
[4]1 M HCl.
[5]ACE from rabbit lung dissolved in HEPES-HCl at a final concentration of 0.33 unit ml$^{-1.}$ Inhibitory activity was calculated according to the following equation:

Inhibitory activity (%)=[($A_{control}-A_{sample}$)/($A_{control}-A_{blank}$)]×110     1 where A represents absorbance. A plot of the inhibitory activity (%) versus $\log_{10}$ of sample concentration (mg powder ml$^{-1}$) was generated using 6 different concentrations of samples for BIPRO™, AS-601 (BiPRO™β-1g), commercial hydrolysates (WPH 917, LE80GF) and of synthetic peptide (f142–148) from β-1g. Each concentration was tested in triplicate and the mean value was plotted in the curves. The $IC_{50}$ value (expressed in terms of mg powder ml$^{-1}$, defined as the concentration of inhibitor which gives 50% inhibition of ACE activity, was calculated using the linear regression equations of the curves.

The linear regression equations corresponding to all the hydrolysates under study are reported in Table 3. The data show that non-hydrolyzed BiPRO™ has very low ACE-inhibitory activity ($IC_{50}$ 380 mg powder. ml-1) in comparison with all other products under study. The highest ACE-inhibitory activity was obtained with synthetic peptide f142–148 of β-1g for which 50% of inhibition was already obtained at the lowest concentration ($IC_{50}$ 0.04 mg powder.ml$^{-1}$). The ACE-inhibitory effectiveness of the hydrolysates under study followed the order: AS-603K (BiPRO™)> AS-605K (BiPRO™)>AS-601 (BiPRO™)>AS-605K (β-1g)>AS-601 (β-1g)>LE80GF>WPH 917.

Table 3, as follows presents the linear regression equations (y=m lnX+b) of the ACE-inhibitory activity curves obtained with synthetic peptide β-1g (f142–148), in comparison with the hydrolysates under study.

TABLE 3

| Sample | Slope m | Y-intercept b | Reg. Coeff. $R^2$ |
|---|---|---|---|
| β-1 g f142–148 | 10.35 | 84.4 | .83 |
| AS-601 (BiPRO ™) | 15.39 | 62.4 | .99 |
| AS-605 (BiPRO ™) | 14.76 | 63.0 | .99 |
| AS-603K (BiPRO ™) | 14.33 | 67.9 | .96 |
| AS-601 (β-1 g) | 17.69 | 51.9 | .98 |
| AS-605 (β-1 g) | 16.98 | 60.7 | .98 |
| WPH 917 (NZMP) | 19.40 | 44.8 | .96 |
| LE80GF (DMV) | 18.01 | 50.7 | .97 |

The values of $IC_{50}$ calculated for all the samples under study are listed in Table 4. The samples of BiPRO™ showed lower ACE-inhibitory activity with an $IC_{50}$ of 376 mg powder.ml$^{-1}$), whereas synthetic peptide f142–148 of β-1g showed the lowest value (0.04 mg powder.ml$^{-1}$). The hydrolysates derived from BiPRO™ or β-1g-rich products all gave lower IC$_{50}$ values (0.29 to 0.90 mg powder.ml$^{-1}$) than the other commercial hydrolysates (0.96 and 1.30 mg powder.ml$^{-1}$). Also the hydrolysates derived from BIPRO™ led to lower IC$_{50}$ values than those derived from the β-1g-rich product (ex. AS-601 $_{BiPRO™}$=0.45 vs AS-601$_{β-1g}$=0.90 mg powder.ml$^{-1}$).

TABLE 4

Values of IC$_{50}$ for various whey protein products

| Sample | Description | IC$_{50}$ (mg powder ml$^{-1}$) |
|---|---|---|
| BiPRO ™ | whey protein isolate | 376.7 |
| AS-601 (BiPRO ™) | hydrolyzed BiPRO ™ | 0.45 |
| AS-601 (β-1 g) | hydrolyzed β-1 g | 0.90 |
| AS-605 (BiPRO ™) | hydrolyzed BiPRO ™, Kosher certified | 0.42 |
| AS-605 (β-1 g) | hydrolyzed β-1 g, Kosher certified | 0.53 |
| AS-603K (BiPRO ™) | Hydrolyzed BiPRO ™, Kosher certified | 0.29 |
| WPH 917 (NZMP) | whey protein hydrolysate | 1.30 |
| LE80GF (DMV) | whey protein hydrolysate | 0.96 |
| β-1 g f142–148 | synthetic peptide | 0.04 |

Discussion

Our observations show that the enzymatic hydrolysis of whey proteins issued from ion-exchange chromatography, such as BiPRO™ whey protein isolate generates hydrolysates having superior ACE-inhibitory activities, compared to commercial hydrolysates prepared with other sources of whey proteins. Moreover, it appears that BIPRO™ whey protein isolate is a better substrate than β-1g-rich product for the preparation of hydrolysates with antihypertensive activity, as seen by the lower IC$_{50}$ values obtained (Table 4) for AS-601, AS-603K and 605K prepared from BiPRO™ whey protein isolate. This observation was unexpected since it was hypothesized that a Ig rich product would offer a higher potential for producing ACE-Inhibiting peptides, especially the fragment β-1g 142–148 liberated by trypsin (Mullally, M. M., Meisel, H., FitzGerald, R. J., 1997. Identification of a novel angiotensin-I-converting enzyme inhibitory peptide corresponding to a tryptic fragment of bovine β-lactoglobulin. FEBS Letters, 402: 99–101). In fact, the hydrolysates having the lowest IC$_{50}$ (0.29 mg powder ml$^{-1}$) were obtained by hydrolysis with bacterial protease (AS-603K) and not with trypsin (AS-601). Altogether, our results suggest the occurrence of a synergistic effect when BiPRO™ whey protein isolate is used as the substrate, but the explanation for this phenomenon is not clear.

BiPRO™ whey protein isolate and others similarly prepared are preferred for a composition with regard to principal protein composition (β-1g, α-1a, etc.), and content of minor proteins (lactoferrin, lactoperoxydase, immunoglobulins) or peptidic fragments (caseinomacropeptides, proteoses peptones, etc.) which may be precursors of the production of peptides with very strong ACE-inhibition activity during enzymatic hydrolysis. Some of these minor proteins may be at a lower concentration in the β-1g-rich product, as a result of the different fractionation conditions.

Also, it must be emphasized that the enzymes used for the preparation of enzymatic hydrolysates from BiPRO™ whey protein isolate (601, 605K and 603K) respectively Trypsin VI, P Amano 6 and Multifect have very different specificities. Trypsin is known to cleave only the peptidic bonds in the vicinity of Arg and Lys, whereas the two other enzymes have a much broader specificity and will lead to a greater number of shorter peptides. The recent work from Abubakar, et al., supra, suggests that short molecules such as tri- and even di-peptides can have an antihypertensive effect. It is clear that the fragments 142–148 and 78–80 of β-1g are not the only ACE-inhibitors responsible for the antihypertensive properties of all whey protein hydrolysates.

The synergistic effect on ACE-inhibitory potential of whey protein hydrolysates when BiPRO™ whey protein isolate is used may also be originating from its low mineral content, especially with regards to divalent cations such as calcium (15–20 meq/kg) or magnesium (<1 meq/kg). These physicochemical conditions may prevent the occurrence of peptide—peptide interactions and therefore preserve the high ACE-inhibitory potential of the hydrolysate. This hypothesis will be further investigated by comparing the mineral composition of BiPRO™ whey protein isolate with that of β-1g-rich product which showed a lower ACE-inhibitory potential.

This study has shown that the enzymatic hydrolysis of BiPRO™ leads to a synergistic effect in terms of ACE-inhibitory potential of the hydrolysates obtained. It appears that the synergy could result from unique compositional characteristics brought by the ion-exchange process in relation with the presence of minor proteins or fragments.

The above description is intended to enable the person skilled in the art to practice the invention. It is not intended to detail all of the possible modifications and variations which will become apparent to the skilled worker upon reading the description. It is intended, however, that all such modifications and variations be included within the scope of the invention which is seen in the above description and otherwise defined by the following claims. The claims are meant to cover the indicated elements and steps in any arrangement or sequence which is effective to meet the objectives intended for the invention, unless the context specifically indicates the contrary.

What is claimed is:

1. A process for preparing an angiotensin-converting enzyme (ACE)-inhibiting composition comprising:
    (a) preparing an aqueous solution of a whey protein fraction and trypsin;
    (b) holding said solution under conditions effective for partially hydrolyzing said whey protein fraction to provide a hydrolysate having increased ACE-inhibiting activity;
    (c) stopping the hydrolyzation; and
    (d) drying said hydrolysate to provide the ACE-inhibiting composition wherein said composition comprises a mixture of peptides having the following molecular weight profile, as determined by HPLC:

| Range (Daltons) | Soluble Peptides |
|---|---|
| >5000 | 50–55% |
| 2000–5000 | 15–20% |
| <2000 | 30–35% |

2. The process according to claim 1 wherein the trypsin is inactivated following hydrolysis.

3. The process according to claim 1 wherein the trypsin is inactivated by heating following hydrolysis.

4. An ACE-inhibiting composition from whey protein as prepared according to claim 1 that comprises a mixture of peptides having the following molecular weight profile, as determined by HPLC:

| Range (Daltons) | Soluble Peptides |
| --- | --- |
| >5000 | 50–55% |
| 2000–5000 | 15–20% |
| <2000 | 30–35% | wherein said composition inhibits ACE.

5. A treatment regimen for a mammal to inhibit angiotensin-converting enzyme (ACE), said regimen comprising:
orally administering to the mammal, the composition of claim 4 in amounts and at intervals effective to reduce ACE activity.

6. The process according to claim 1, wherein said whey protein fraction is a whey protein isolate.

7. The process according to claim 1, wherein said reaction is stopped when the degree of hydrolysis is within the range of from 5.5 to 6.5%.

8. The process according to claim 1, wherein said whey protein fraction is produced by ion exchange and is characterized by a protein content of at least 94% and an ash content of less than 3%.

9. The process according to claim 8, wherein said reaction is stopped when the degree of hydrolysis is within the range of from 5.5 to 6.5%.

10. A process for preparing an angiotensin-converting enzyme (ACE)-inhibiting composition comprising:
(a) preparing an aqueous solution of a whey protein fraction produced by ion exchange and trypsin;
(b) holding said solution under conditions effective for partially hydrolyzing said whey protein fraction to provide a hydrolysate having increased ACE-inhibiting activity;
(c) stopping the hydrolyzation when a degree of hydrolysis is reached within the range of from 5.5 to 6.5%, wherein said hydrolysate comprises a mixture of peptides having the following Molecular Weight Profile, as determined by HPLC:

| Range (Daltons) | Soluble Peptides |
| --- | --- |
| >5000 | 50–55% |
| 2000–5000 | 15–20% |
| <2000 | 30–35%; and |

(d) drying said hydrolysate to provide the ACE-inhibiting composition.

11. A process for preparing an angiotensin-converting enzyme (ACE)-inhibiting composition comprising:
(a) preparing an aqueous solution of trypsin and whey protein fraction, prepared by ion exchange processing and characterized by a protein content of at least 94% and an ash content of less than 3%;
(b) holding said aqueous solution under conditions effective for partially hydrolyzing said whey protein fraction to provide a hydrolysate;
(c) stopping said hydrolyzation to provide a hydrolysate solution; and
(d) drying said hydrolysate solution prepared in step c to provide the ACE-inhibiting composition, wherein said composition comprises a mixture of peptides having the following molecular weight profile, as determined by HPLC:

| Range (Daltons) | Soluble Peptides |
| --- | --- |
| >5000 | 50–55% |
| 2000–5000 | 15–20% |
| <2000 | 30–35% |

12. The process according to claim 11, wherein said reaction is stopped when the degree of hydrolysis is within the range of from 5.5 to 6.5%.

13. The process according to claim 1 or 10, wherein the whey protein fraction has an ash content of <3%.

14. The process according to claim 1, 10, or 11, wherein the whey protein faction has a mineral content of calcium of 15–20 meq/kg.

15. The process according to claim 1, 10, or 11, wherein the whey protein fiction has a mineral content of magnesium of <1 meq/kg.

16. The process according to claim 1 or 10, wherein the whey protein fraction has a protein content of at least 35%.

17. The process according to claim 1 or 10, wherein the whey protein fraction has a protein content that varies by 0 to 25% from 97.5±1.0%.

18. The process according to claim 1 or 10, wherein the whey protein fraction has a protein content that varies by 5 to 10% from 97.5±1.0%.

19. The process according to claim 1, 10, or 11, wherein the whey protein fraction has a protein content that varies less than 5% from 97.5±1.0%.

20. The process according to claim 1, 10, or 11 wherein the whey protein fraction has a protein content of 97.5±1.0

21. The process according to claim 1, 10, or 11 wherein the whey protein fraction is characterized as follows:

| Analysis | Specification | Typical Range |
| --- | --- | --- |
| Moisture (%) | 5.0 max | 4.7 ± 0.2 |
| Protein, dry basis (N × 6.38) (%) | 95.0 min. | 97.5 ± 1.0 |
| Fat (%) | 1.0 max | 0.6 ± 0.2 |
| Ash (%) | 3.0 max | 1.7 ± 0.3 |
| Lactose (%) | 1.0 max | <0.5 |
| pH | 6.7–7.5 | 7.0 ± 0.2 |

22. The process according to claim 10 or 11, wherein the whey protein fraction is a whey protein isolate.

23. The process according to claim 1, 10, or 11, wherein the trypsin is porcine trypsin.

24. The process according to claim 1, 10, or 11, further comprising concentrating said hydrolysate.

25. The process according to claim 1 or 10, wherein they hydrolysate is spray-dried.

26. The process according to claim 1, wherein the whey protein fraction is prepared by ion-exchange processing.

27. The process according to claim 1, wherein said reaction is stopped when the degree of hydrolysis is within the range of from 11.0–12.5%.

28. The process according to claim 1, wherein said reaction is stopped when the degree of hydrolysis is within the range of from 19.5–20.5%.

29. An ACE-inhibiting composition from whey protein as prepared according to claim 10, 11 or 30 that comprises a mixture of peptides having the following molecular weight profile, as determined by HPLC:

| Range (Daltons) | Soluble Peptides |
|---|---|
| >5000 | 50–55% |
| 2000–5000 | 15–20% |
| <2000 | 30–35% | wherein said composition inhibits ACE.

30. A process for preparing an angiotensin-converting enzyme (ACE)-inhibiting composition comprising;
  (a) preparing an aqueous solution of a whey protein isolate and trypsin;
  (b) holding said aqueous solution under conditions effective for partially hydrolyzing said whey protein isolate;
  (c) stopping said hydrolyzation to provide a hydrolysate solution; and
  (d) drying said hydrolysate solution prepared in step c to provide the ACE-inhibiting composition, wherein the composition comprises a mixture of peptides having the following molecular weight profile, as determined by HPLC:

| Range (Daltons) | Soluble Peptides |
|---|---|
| >5000 | 50–55% |
| 2000–5000 | 15–20% |
| <2000 | 30–35% |

31. The process according to claim 30, wherein the whey protein isolate has a protein content that varies by 0 to 25% from 97.5%.

32. The process according to claim 30, wherein the whey protein isolate has a protein content of at least 94%.

33. The process according to claim 30, wherein the whey protein isolate contains at least 70% β-lactoglobulin.

34. The process according to claim 33, wherein the whey protein isolate contains at least 80% β-lactoglobulin.

35. The process according to claim 34, wherein the whey protein isolate contains about 91% β-lactoglobulin.

36. A treatment regimen for a mammal to inhibit angiotensin-converting enzyme (ACE), said regimen comprising:
  orally administering to the mammal, the composition of claim 29 in amounts and at intervals effective to reduce ACE activity.

* * * * *